(12) United States Patent
Schermeier et al.

(10) Patent No.: US 8,518,025 B2
(45) Date of Patent: Aug. 27, 2013

(54) SYSTEM FOR CLEARING MODES OF OPERATION ON A MULTICOMPONENT MEDICAL INSTRUMENT

(75) Inventors: Olaf Schermeier, Lübeck (DE); Marita Kalfke, Lübeck (DE); Andreas Otto, Bargteheide (DE); Gerd Wotha, Warnsdorf (DE)

(73) Assignee: Dräger Medical GmbH, Lübeck (DE)

( * ) Notice: Subject to any disclaimer, the term of this patent is extended or adjusted under 35 U.S.C. 154(b) by 1070 days.

(21) Appl. No.: 12/094,676

(22) PCT Filed: Jun. 16, 2006

(86) PCT No.: PCT/EP2006/005779
§ 371 (c)(1),
(2), (4) Date: May 22, 2008

(87) PCT Pub. No.: WO2007/059810
PCT Pub. Date: May 31, 2007

(65) Prior Publication Data
US 2008/0319426 A1    Dec. 25, 2008

(30) Foreign Application Priority Data

Nov. 26, 2005  (DE) .......................... 10 2005 056 477

(51) Int. Cl.
*A61B 17/00* (2006.01)
(52) U.S. Cl.
USPC ............................. 606/1; 604/65
(58) Field of Classification Search
USPC ............................. 604/65; 606/1
See application file for complete search history.

(56) References Cited

U.S. PATENT DOCUMENTS

| 4,949,072 | A  | * | 8/1990  | Comerford et al. ........... 340/525 |
| 5,687,717 | A  |   | 11/1997 | Halpern et al. |
| 6,162,180 | A  | * | 12/2000 | Miesel et al. ................. 600/481 |
| 6,406,426 | B1 | * | 6/2002  | Reuss et al. .................... 600/300 |
| 2001/0020148 | A1 |   | 9/2001 | Sasse et al. |
| 2003/0093503 | A1 | * | 5/2003 | Yamaki et al. ................ 709/220 |
| 2004/0127937 | A1 |   | 7/2004 | Newton |
| 2004/0171982 | A1 |   | 9/2004 | Danchin |
| 2004/0210151 | A1 |   | 10/2004 | Tsukashima et al. |
| 2004/0267297 | A1 |   | 12/2004 | Malackowski |
| 2005/0097191 | A1 | * | 5/2005 | Yamaki et al. ................ 709/219 |
| 2005/0115561 | A1 | * | 6/2005 | Stahmann et al. ....... 128/200.24 |

FOREIGN PATENT DOCUMENTS

| DE | 297 14 826 U1 | 12/1998 |
| DE | 198 09 952 A1 | 9/1999 |
| DE | 101 16 361 A1 | 10/2002 |
| DE | 101 16 650 A1 | 11/2002 |
| DE | 102 45 140 A1 | 4/2004 |

(Continued)

*Primary Examiner* — Bill Thomson
*Assistant Examiner* — Jeffrey Lipitz
(74) *Attorney, Agent, or Firm* — McGlew and Tuttle, P.C.

(57) ABSTRACT

A system is provided for clearing modes of operation on a multicomponent medical instrument with a basic instrument (1) and at least one connectable accessory instrument (4) for the basic instrument (1). The accessory instrument (4) is equipped with a wireless, readable data memory (2) for modes of operation of the medical instrument and the basic instrument (1) has a reading unit (3) for the data memory (2). The reading unit (3), when the accessory instrument (4) is connected, reaches a sending/receiving range for reading out the data.

20 Claims, 1 Drawing Sheet

(56) References Cited

FOREIGN PATENT DOCUMENTS

| EP | 1 347 638 A1 | 9/2003 |
| EP | 1 516 641 A | 3/2005 |
| EP | 1 579 884 A1 | 9/2005 |

* cited by examiner

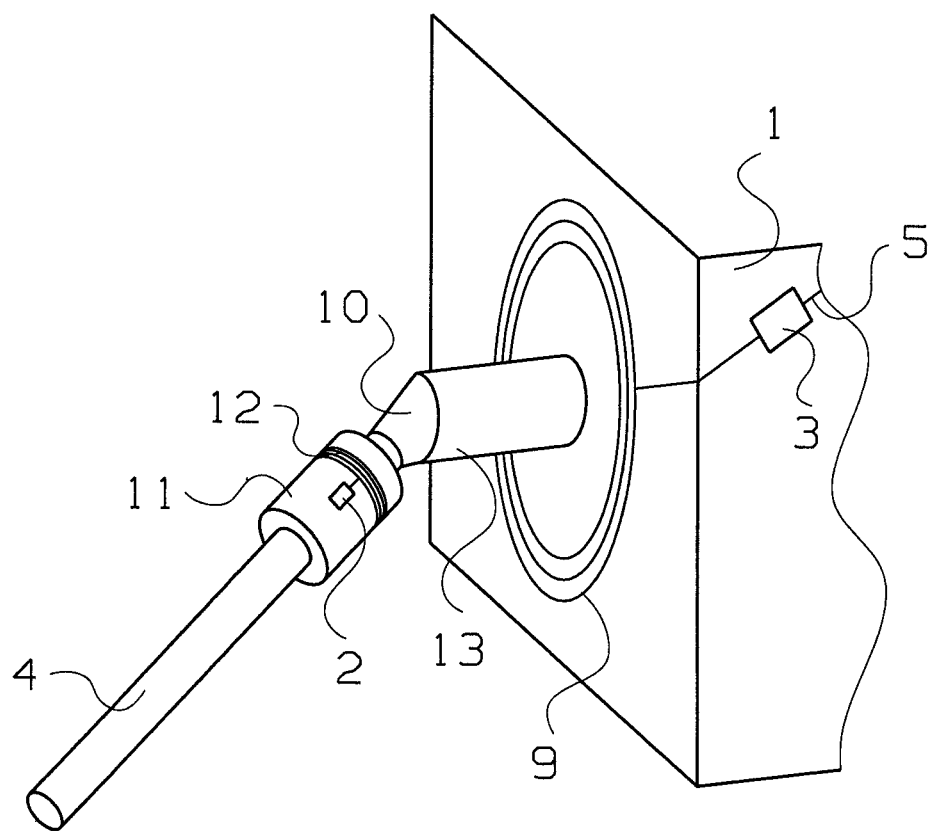

SYSTEM FOR CLEARING MODES OF OPERATION ON A MULTICOMPONENT MEDICAL INSTRUMENT

CROSS REFERENCE TO RELATED APPLICATIONS

This application is a United States National Phase application of International Application PCT/EP2006/005779 and claims the benefit of priority under 35 U.S.C. §119 of German Patent Application DE 10 2005 056 477.1 filed Nov. 26, 2005, the entire contents of which are incorporated herein by reference.

FIELD OF THE INVENTION

The present invention pertains to a system for clearing modes of operation on a multicomponent medical instrument. The modes of operation are functions, which are already implemented or will be implemented at a future time in the software of a medical instrument, for example, an anesthesia apparatus or respirator.

BACKGROUND OF THE INVENTION

A mode of operation corresponds, for example, to a certain mode of artificial respiration, such as NIV®, AutoFlow®, SmartCare®. When purchasing corresponding medical instruments, a user usually has to determine which modes of operation, i.e., respiration (also referred to as ventilation) will be available to him. If the requirement profile on the medical instrument changes, i.e., if additional modes of respiration are desired at a later time or if modes of respiration already present prove to be no longer necessary, then the corresponding software modification has to be made previously on the instrument itself. The providing of this service on site is associated with additional effort and costs.

Clearing or blocking modes of operation via an external, separate storage medium in the form of a chip card has become known from DE 101 16 650 B4.

SUMMARY OF THE INVENTION

The object of the present invention is to provide a system, which has been improved in relation to the manageability in practical use, for clearing modes of operation on a multicomponent medical instrument, which are especially associated with an individual patient.

According to the invention, a system is provided for clearing modes of operation on a multicomponent medical instrument with a basic instrument and at least one connectable accessory instrument for the basic instrument. The accessory instrument is equipped with a wireless, readable data memory with data representing modes of operation of the instrument. The basic instrument is equipped with a reading unit for the data memory which, when the accessory instrument is connected, reaches a sending/receiving range for reading out the data.

A multicomponent medical instrument consists of the basic instrument and one or more accessory instruments or accessory parts, which are necessary for the operation of the medical instrument. Accessory instruments for a basic instrument in the form of an anesthesia apparatus or respirator are, for example, breathing tubes, breathing masks, respiration humidifiers, filters, measuring units, $CO_2$ absorbers, which are especially patient-individual accessory instruments, which are used for a certain patient and are generally disposed of after use.

The modes of operation are cleared in such a way that, in case of proper mechanical connection of an accessory instrument to the basic instrument, the data memory of the accessory instrument with the readable data reaches the sending and receiving range of the reading unit of the basic instrument for the wireless reading of the data from the data memory. The data memory is especially a transponder, i.e., a receiving-sending unit, which operates according to the polling-reply system. A coded polling signal, received by the transponder by means of an antenna, is decoded and analyzed according to the identification key and optionally other information of the polling reading unit. As a result, a coded reply signal, selectively intended for the polling reading unit, is automatically transferred in a wireless manner by the transponder with the desired data for modes of operation to be cleared and optionally with additional patient-individual additional data. The data are likewise automatically decoded and analyzed in the reading unit of the basic instrument.

A time or a duration of availability can be set for each of the individual cleared modes of operation in the medical instrument, for example, in the form of a time account kept for each cleared mode of operation, to which time units can be debited.

In a special embodiment, the data memory in the accessory instrument may also be writable and the complementary reading unit in the basic instrument may be combined with a writing unit for the data memory.

The accessory instrument that can be mechanically connected to the basic instrument is especially a specific accessory part, which is intended for one-time use and anyway is connected to the basic instrument by the instrument user for the proper operation of the medical instrument.

Before the mechanical connection of the accessory instrument, i.e., for example, a breathing tube, a breathing mask, a filter, or a respiration humidifier, the basic instrument, especially an anesthesia apparatus or respirator, is in its basic configuration, i.e., certain optional modes of operation are not yet cleared. If now the special accessory instrument is connected for a one-time use intended for an individual patient, then the operation of certain modes of operation especially associated with an individual patient is cleared for the duration of the connection to the basic instrument. If the specific accessory instrument is again removed from the basic instrument, then the optional modes of operation are no longer available. If the specific, patient-individual accessory instrument is connected to another basic instrument, e.g., if the patient is located at another basic instrument, then the optional modes of operation are optionally available at the another basic instrument. Optionally, a certain running time or duration of use may be associated with the accessory instrument or accessory part, after which the clearing expires, for example, after a certain number of operating hours. Thus, medical instruments can be configured on an individual patient basis. In addition, based on the data collected, the total costs of the usage can be determined on an individual patient basis, without the handling of the instruments being changed.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which preferred embodiments of the invention are illustrated.

BRIEF DESCRIPTION OF THE DRAWING

In the drawing:

The sole FIGURE is a schematic representation showing an anesthesia apparatus or respirator in the area of a gas-supplying interface between a basic instrument and an accessory instrument in the form of a breathing tube.

DESCRIPTION OF THE PREFERRED EMBODIMENT

Referring to the drawing in particular, the sole schematic FIGURE shows an anesthesia apparatus or respirator in the area of a gas-supplying interface between the basic instrument 1 and an accessory instrument 4 in the form of a breathing tube. The breathing gas connection has a variable-angle male connector 10. The breathing tube is connected to this connector 10 by a sealing socket 11 being connected to the male connector 10 as a female connector.

A transponder has a digital electronic data memory 2 with an antenna 12 that is especially injection molded into the socket 11 such that its windings are directed at right angles to the axis of the tube connection. Another antenna 9 of a reading unit 3 on the basic instrument side, which is optionally combined with a writing unit, is arranged essentially at right angles to the axis of the part of the breathing gas connection 13 which is rigidly connected to the basic instrument 1. In this way, the result is that with the accessory instrument properly connected to the basic instrument 1 in all positions of the variable-angle male connector 10, the fields, which form about the antennas 9, 12, have a parallel component each in relation to the receiving antenna, so that a sufficient inductive coupling is given for the wireless transmission of signals and data.

The digital electronic data memory 2 contains information about the modes of operation that are to be cleared, for example, modes of respiration, and information on how long these modes are cleared with the corresponding accessory instrument. The data memory 2 is connected to the socket 11 by means of bonding, welding or injection molding. After use, the breathing tube is disposed of together with the transponder. The data in the data memory 2 are coded, such that the information cannot be manipulated. The reading unit 3 in the basic instrument 1 reads in the data via at least one or more antennas 9, decodes them and analyzes them. Depending on the analysis, the modes of operation, especially modes of respiration, are cleared in the medical instrument.

If a conventional accessory is connected, the additional functions are not provided on the medical instrument. Besides the data mentioned, further patient-individual or accessory-instrument-individual information can be stored in the data memory 2.

The reading unit 3 is connected to the electronics of the basic instrument 1 via a line 5.

The data in the data memory 3 are especially coded by means of a code during manufacture, and the reading unit is equipped with a symmetrical key for decoding the data. The coded polling signal, received by the transponder by means of the antenna 9, is decoded and analyzed according to the identification key and optionally other information of the polling reading unit. As a result, a coded reply signal, selectively intended for the polling reading unit, is automatically transferred in a wireless manner by the transponder with the desired data for modes of operation to be cleared and optionally with additional patient-individual additional data. The data are likewise automatically decoded and analyzed in the reading unit of the basic instrument.

While a specific embodiment of the invention has been shown and described in detail to illustrate the application of the principles of the invention, it will be understood that the invention may be embodied otherwise without departing from such principles.

The invention claimed is:

1. A system for clearing modes of operation on a multi-component medical instrument, the system comprising:
    a basic instrument;
    a connectable accessory instrument for operative connection to said basic instrument;
    a wireless, readable data memory unit with modes of respiration operation data of said connectable accessory instrument, said respiration operation data including operation duration data of said connectable accessory instrument, said connectable accessory instrument being equipped with said wireless, readable data memory unit; and
    a reading unit for reading said wireless, readable data memory unit, said reading unit reading data of said wireless, readable memory unit for receiving said modes of respiration operation data of said connectable accessory instrument when said connectable accessory instrument is connected to said basic instrument, said connectable accessory instrument being in a sending/receiving range for reading out the operation data when said connectable accessory instrument is connected to said basic instrument, said basic instrument being equipped with said reading unit, said reading unit analyzing said operation data when said connectable accessory instrument is connected to said basic instrument such that said reading unit clears at least one of said modes of respiration operation data, said basic instrument executing at least one mode of respiration with said connectable accessory instrument based on said at least one of said cleared modes of respiration operation data.

2. A system in accordance with claim 1, wherein said wireless, readable data memory unit of said connectable accessory instrument comprises data associated with an individual patient, which comprise at least one respiration mode of operation for the patient.

3. A system in accordance with claim 1, wherein said wireless, readable data memory unit of said connectable accessory instrument comprises data entries characteristic of said connectable accessory instrument, so that modes of respiration operation characteristic only of said connectable accessory instrument are cleared in the basic instrument, including modes of respiration operation that are associated with an individual patient.

4. A system in accordance with claim 2, wherein said basic instrument is an anesthesia apparatus or respirator, and said connectable accessory instrument is a breathing tube, a breathing mask, a filter, or a respiration humidifier.

5. A system in accordance with claim 1, wherein said wireless, readable data memory unit is a transponder.

6. A system in accordance with claim 4, wherein the modes of respiration operation are software modules for respiration processes of said anesthesia apparatus or respirator, said anesthesia apparatus or respirator executing said software modules when said anesthesia apparatus or respirator clears at least one of said modes of respiration operation data.

7. A system in accordance with claim 1, wherein said reading unit is combined with a writing unit and data is written to said wireless, readable data memory unit via said writing unit.

8. A system in accordance with claim 7, wherein after clearing a mode of operation on the basic instrument, data characteristic of the clearing are written to said wireless, readable data memory unit via said writing unit.

9. A system in accordance with claim 1, wherein said modes of respiration operation are cleared via said reading unit for the duration of the connection of said basic unit to said connectable accessory instrument such that said at least one mode of respiration is executed until said basic unit is disconnected from said connectable accessory instrument.

10. A system in accordance with claim 1, wherein said reading unit clears said modes of respiration operation for a time set in said wireless, readable data memory unit based on said operation duration data and/or a set duration based on said operation duration data.

11. A system in accordance with claim 1, wherein one or more currently active modes of respiration operation is deactivated by means of said wireless, readable data memory unit.

12. A system in accordance with claim 1, wherein the data in said wireless, readable data memory of said connectable accessory instrument are coded and said reading unit is equipped with a complementary, symmetrical key for decoding the data, said reading unit decoding said data in said wireless, readable data memory with said symmetrical key.

13. A system in accordance with claim 1, wherein said connectable accessory instrument is a disposable article for one-time use on the patient.

14. A medical system for clearing modes of operation on a multicomponent medical instrument, the medical system comprising:
   a basic instrument;
   a connectable accessory instrument for physical connection to said basic instrument;
   a transponder with a readable data memory with modes of respiration operation data of said connectable accessory instrument and with an antenna for wireless communication, said connectable accessory instrument being connected to said transponder, said modes of respiration operation data comprising operating time period data associated with one or more modes of respiration for said connectable accessory instrument; and
   a reading unit with an antenna having a sending/receiving range, said reading unit receiving said modes of respiration operation data from said readable data memory via said transponder when said connectable accessory instrument is mechanically connected to said basic instrument, said readable data memory being within said sending/receiving range when said basic unit is connected to said connectable accessory instrument, said basic instrument being provided with said reading unit, said reading unit processing said modes of respiration operation data such that said reading unit authorizes a use of at least one of said modes of respiration operation data and said reading unit determines an operating time period of said connectable accessory instrument based on said operating time period data, said basic unit and said connectable accessory instrument executing at least one mode of respiration for said operating time period based on said authorized at least one of said modes of respiration operation data.

15. A system in accordance with claim 14, wherein said modes of respiration operation data of said readable data memory of said connectable accessory instrument includes individual patient data, which comprise at least one mode of operation for the patient.

16. A system in accordance with claim 14, wherein said readable data memory of said connectable accessory instrument includes accessory instrument characteristic data restricting modes of respiration operation of said connectable accessory instrument or restricting modes of respiration operation to modes of respiration operation associated with an individual patient.

17. A system in accordance with claim 14, wherein said basic instrument is an anesthesia apparatus or respirator, and said connectable accessory instrument is a breathing tube, a breathing mask, a filter, or a respiration humidifier and the modes of operation are software modules for respiration processes of an anesthesia apparatus or respirator, said anesthesia apparatus or respirator executing said software modules after said reading unit clears said at least one of said modes of respiration operation data.

18. A system in accordance with claim 14, wherein said reading unit further comprises a writing unit and said readable data memory is written to via said writing unit, wherein after clearing a mode of operation on the connectable accessory instrument, data characteristic of the clearing are written to said readable data memory via said writing unit and said modes of operation are cleared for one of a duration of the connection of said connectable accessory instrument with said basic unit and for a time set in said readable data memory and/or a set duration.

19. A system in accordance with claim 14, wherein the data in said readable data memory of said connectable accessory instrument are coded and said reading unit is equipped with a complementary, symmetrical key for decoding the data, said reading unit decoding said data in said readable data memory with said symmetrical key.

20. A system in accordance with claim 14, wherein said connectable accessory instrument is a disposable article for one-time use on the patient.

\* \* \* \* \*

UNITED STATES PATENT AND TRADEMARK OFFICE
CERTIFICATE OF CORRECTION

| | | |
|---|---|---|
| PATENT NO. | : 8,518,025 B2 | |
| APPLICATION NO. | : 12/094676 | |
| DATED | : August 27, 2013 | |
| INVENTOR(S) | : Olaf Schermeier et al. | |

It is certified that error appears in the above-identified patent and that said Letters Patent is hereby corrected as shown below:

On the title page, item (75), Inventors "Kalfke," should read

-- Klafke, --

Signed and Sealed this
Fifteenth Day of October, 2013

Teresa Stanek Rea
*Deputy Director of the United States Patent and Trademark Office*